United States Patent [19]

Wallace et al.

[11] Patent Number: 5,516,406
[45] Date of Patent: May 14, 1996

[54] PROCESS FOR PURIFYING ACIDS FORMED DURING LIQUID PHASE OXIDATION OF BUTANE

[75] Inventors: Nicole G. Wallace; Kenneth A. Windhorst, both of Pampa, Tex.

[73] Assignee: Hoechst Celanese Corporation, Somerville, N.J.

[21] Appl. No.: 356,610

[22] Filed: Dec. 15, 1994

[51] Int. Cl.$^6$ .............................. B01D 3/34; C07C 51/42
[52] U.S. Cl. .................. 203/34; 203/16; 203/35; 203/37; 203/38; 203/71; 562/608; 562/609
[58] Field of Search ................... 203/15, 16, 34, 203/35, 33, 36, 37, 38, 71; 562/608, 606, 609

[56] References Cited

U.S. PATENT DOCUMENTS

| | | | |
|---|---|---|---|
| 2,138,582 | 11/1938 | Knapp | 562/608 |
| 2,255,421 | 9/1941 | Groll et al. | 203/34 |
| 2,273,459 | 2/1942 | Britton et al. | 562/608 |
| 3,196,176 | 7/1965 | Howell | 203/35 |
| 3,347,756 | 10/1967 | Snell | 203/32 |
| 4,110,372 | 8/1978 | Hey et al. | 562/608 |
| 4,131,742 | 12/1978 | Hudson | 562/506 |

*Primary Examiner*—Wilbur Bascomb, Jr.
*Attorney, Agent, or Firm*—Donald R. Cassady

[57] ABSTRACT

A method of purifying the oxidate product formed by the liquid phase oxidation of $C_4$–$C_8$ paraffinic hydrocarbons comprises adding a strong acid catalyst to the oxidate product to catalyze the break down of Michael addition products of unsaturated carbonyls and carboxylic acids so that the carbonyls can be distilled off during the initial stages of purification.

15 Claims, 1 Drawing Sheet

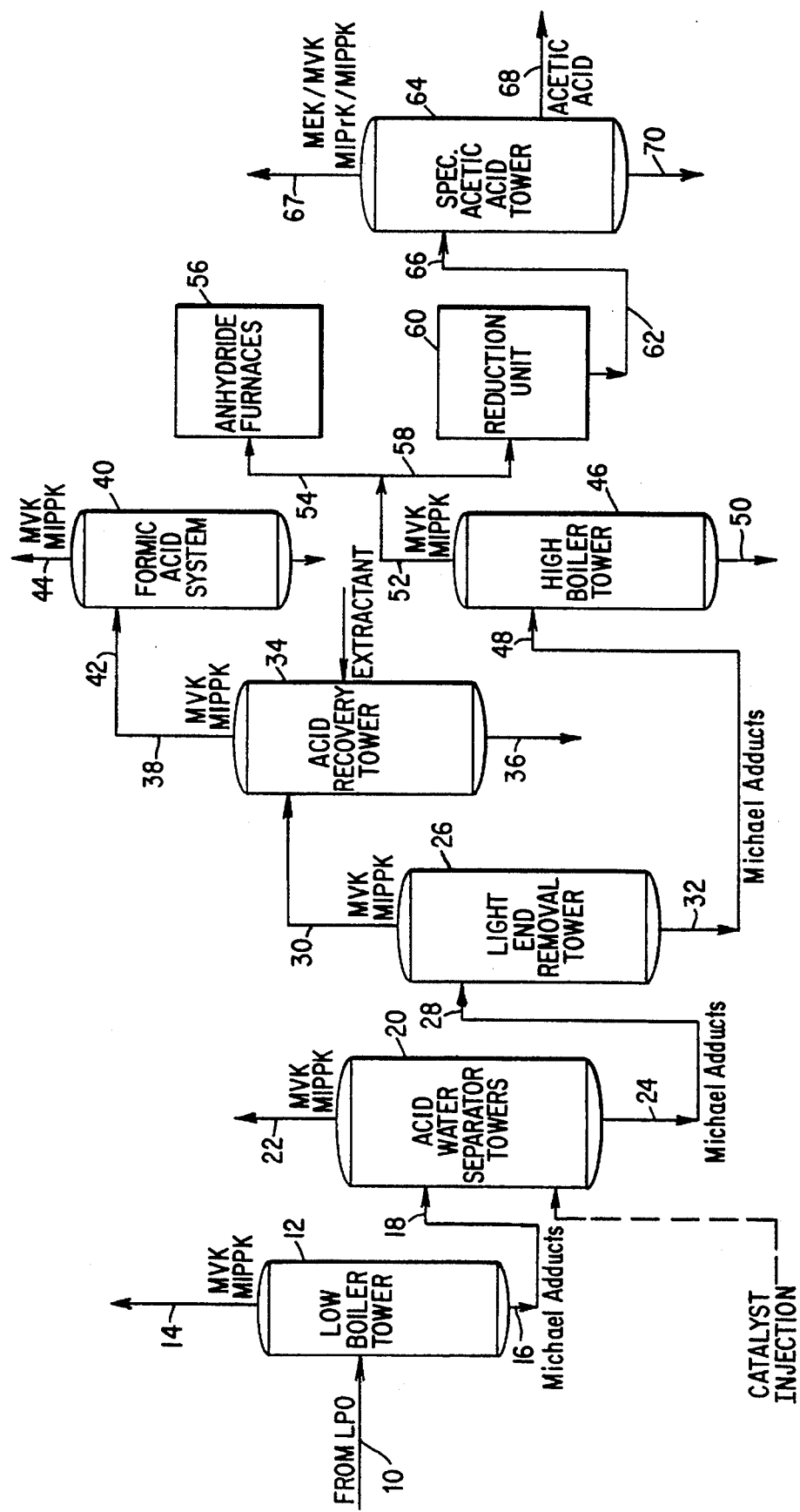

PROCESS FOR PURIFYING ACIDS FORMED DURING LIQUID PHASE OXIDATION OF BUTANE

BACKGROUND OF THE INVENTION

This invention relates to a process for the oxidation of butane in the liquid phase whereby valuable oxygenated organic compounds are produced. It is particularly related to a process for the production of aliphatic monocarboxylic acids such as acetic acid by the oxidation of butane in the liquid phase whereby impurities in the acids which adversely effect the permanganate time thereof are removed by a novel process.

Direct oxidation of saturated aliphatic hydrocarbons such as propane, butane, pentane, hexane, heptane or mixtures of the hydrocarbons, with oxygen is well known. In particular, the oxidation of butane is a well-known process which has been described in numerous patents and technical publications relating to both liquid phase and vapor phase oxidation both catalytically and non-catalytically. Liquid-phase catalytic oxidation (LPO) of n-butane was introduced by Celanese in 1952 in Pampa, Tex. The oxidation product during liquid phase oxidation of paraffin hydrocarbons such as butane contains a light ends boiling up to about 99° C., water, aliphatic monocarboxylic acids of 1–4 carbon atoms and high boiling residues. The major low-boiling constituents are ethyl acetate, methyl ethyl ketone and methyl vinyl ketone, along with traces of aldehydes and other esters. The acids which are produced include mainly formic acid and acetic acid with smaller amounts of propionic acid, acrylic acid and butyric acid. A number of carbonyl compounds form the higher substances. To recover the acetic acid and other acids from the oxidate product, a series of distillation steps are utilized. Unfortunately, the acetic acid and other acids produced in such a way have not always passed the various tests for permanganate time. Since a sufficient permanganate time is an important commercial test which the acid product must meet for many uses, the presence therein of impurities which degrade permanganate time is highly objectionable.

It has been known that small amounts of unsaturated ketones, e.g. methyl vinyl ketone and methyl isopropenyl ketone are present in the acid products and are the cause of the permanganate time reductions which have been found. This discovery is described in U.S. Pat. No. 3,347,756. As stated in this patent, the unsaturated ketones are capable of reacting reversibly with acids to form addition products which, unlike the parent ketones, are saturated and higher boiling than the $C_1$–$C_4$ acids. The presence of the addition product between the unsaturated ketones and the acids in the final acid products has no effect on the permanganate time. The failure of the recovered acids to pass the test for permanganate time, however, is due to the presence of traces of the unsaturated ketones, in spite of one or more fractional distillation steps.

The rate of cracking of the addition products and of recombination of methyl vinyl ketone and acids depends upon temperature, the acid present and the concentrations of methyl vinyl ketone, acids and addition products. Formic acid reacts faster than acetic acid. Substantial recombination of methyl vinyl ketone and formic acid will occur even in 5 minutes at 90° C. when excess formic acid is present.

It is now known that the unsaturated carbonyl compounds such as methyl vinyl ketone and methyl isopropenyl ketone can react with the acids in a number of ways such as condensation, polymerization and addition reactions. One particular type of addition reaction, Michael addition, involves the addition of an organic acid or something similar across the carbon-carbon double bond of the unsaturated ketone. The reaction is acid or base catalyzed and is reversible. In the case of methyl vinyl ketone and acetic acid, the reactants are much lower boiling than the product of 4-acetoxy-2-butanone (80 ° C. and 118° C. verses 190° C.). The differences in boiling temperature, along with the reversibility of the Michael addition, dictates that the equilibrium between product and reactants can be shifted by temperature. For example, if the temperature is greater than the boiling point of the methyl vinyl ketone, the methyl vinyl ketone would tend to be preferentially removed from the system as a vapor. To maintain equilibrium, some 4-acetoxy-2-butanone will revert back to methyl vinyl ketone and acetic acid. Accordingly, as long as methyl vinyl ketone or acetic acid are removed from the system, the 4-acetoxy-2-butanone will revert back to the reactants.

In previously mentioned U.S. Pat. No. 3,347,756 there is described a process for the removal of methyl vinyl ketone addition products from the acetic acid-containing LPO reaction mixture by a heat treatment process at such a temperature to shift the equilibrium and to substantially decompose the addition product into methyl vinyl ketone and the product acid. The removal may be effected by distilling the mixture to take off acetic acid and methyl vinyl ketone produced by cracking the addition product and leaving the uncracked portion of the addition product in the residue. This process, however, simply leaves a very valuable residue which is typically disposed of and still contains acetic acid product. U.S. Pat. No. 3,347,756 proposed that the separation of the liberated methyl vinyl ketone from the acetic acid-containing distillate may be effected by a variety of methods including fractional distillation or hydrogenation into a compound such as methyl ethyl ketone or secondary butanol which do not condense with acetic acid readily and which may subsequently be removed from the acetic acid. These separation techniques are difficult since it is not easy to remove the minor amounts of methyl vinyl ketone from the acetic acid by distillation. Secondly, the reaction with hydrogen does not convert all the methyl vinyl ketone and some remains to degrade the acid products. Thus, while the process disclosed in U.S. Pat. No. 3,347,756 has been useful, it is not sufficient to completely alleviate the degradation of permanganate time.

It has been found that the unsaturated ketones such as the methyl vinyl ketone and methyl isopropenyl ketone are formed during the LPO reaction and react with the acid products including acetic acid by Michael addition in the LPO reactor. The Michael adducts breakdown thermally to the unsaturated and acid components slowly such that the adducts are carried along with the acid products downstream during purification. This causes serious quality problems not only in the acetic acid but in ethyl acetate, formic acid, propionic acid, butyric acid and acetic anhydride purification. While eventually the adducts are removed as bottoms from the acid product, this results in two disadvantages. For one, there is always some reverse reaction which means that the unsaturated ketones are present in the final acid product. Secondly, the adducts contain a substantial amount of tied up acids and if these bottoms are burned, this results in an unnecessary waste.

Accordingly, it is an object of the present invention to improve the quality of acid products formed during the liquid phase oxidation of saturated aliphatic hydrocarbons.

Another object of the invention is to provide for the removal of unsaturated compounds from LPO acids which degrade the permanganate time of the acids.

Still another object of the invention is to provide a process for purifying LPO acids by breaking down the adducts which form between the acids and unsaturated ketone compounds during the LPO reaction in the initial stages of purification so that the unsaturated compounds can be removed prior to final acid product purification.

Still yet another object of the invention is to enhance the breakdown of Michael adducts formed by the addition reaction of acids to unsaturated ketones produced during liquid phase oxidation of saturated aliphatic hydrocarbons so that the unwanted unsaturated ketones can be removed form the acid products during the early stages of purification and additional acids can be freed from the Michael adducts.

SUMMARY OF THE INVENTION

The LPO process for oxidizing saturated aliphatic hydrocarbons such as butane produces many unsaturated carbonyl compounds such as methyl vinyl ketone (MVK) and methyl isopropenyl ketone (MIPPK) as part of the product mix which includes organic acids. The unsaturated compounds react with the organic acids to form addition products such as Michael adducts. For example, 4-acetoxy-2-butanone is the Michael adduct of MVK and acetic acid. These Michael adducts are present throughout the LPO reaction system starting with the LPO reactor product and continuing through the crude acid streams during the purification treatment. These Michael adducts break down thermally to their unsaturated ketone and acid components slowly and thus, are the reason why these adducts are carried throughout the LPO reaction and purification system. The unsaturated compounds reformed during the thermal breakdown of the Michael adducts cause quality problems in the acid products formed in the LPO reactor including acetic acid, formic acid, etc.

In accordance with the present invention a strong acid catalyst is added to the LPO reaction products to catalyze the break down of nearly all of the Michael adducts at the beginning of the crude acid purification process to allow for the removal of the unsaturated compounds before such compounds are carded downstream during purification and cause quality problems in the final acid products. Sulfonic acid catalysts have been shown to readily break down the Michael adducts to the corresponding unsaturated ketone and acid substituents whereby the lighter unsaturated ketones can be distilled off early on in the purification process to eliminate the downstream contamination of the crude acid streams. By breaking down the Michael adducts early in the purification process, not only are the unsaturated compounds distilled off but the adducts are not carded downstream. Accordingly, the acid products are free of the unsaturated compounds which degrade the permanganate time and further, additional acid is produced by the breakdown of the adducts.

BRIEF DESCRIPTION OF THE DRAWING

The FIGURE is a schematic diagram illustrating the process of the present invention to purify an LPO reaction product.

DETAILED DESCRIPTION OF THE INVENTION

The process of the present invention can be seen by referring to the FIGURE which illustrates the general purification process of the present invention. The purification process of the present invention is particularly concerned with purifying the oxidation product obtained by the liquid phase oxidation of $C_4$ to $C_8$ paraffin hydrocarbons. In particular, the process can be explained by referring to the purification of the oxidation product obtained by the liquid oxidation of butane and, more specifically, the purification of acetic acid and other acid products by such oxidation. The specifics of the liquid phase oxidation, whether catalytic or non-catalytic is not particularly relevant to the purification process and, accordingly, any liquid phase oxidation reaction consistent with the above general reaction directed to oxidizing saturated aliphatic hydrocarbons can be used as such general reaction produces a mixed oxidate product. Referring to the FIGURE, which although illustrating the liquid oxidation of butane specifically, is applicable to the liquid phase oxidation of higher paraffins. The oxidation product from the LPO reactor, such as for example produced by the oxidation of butane, is introduced via line 10 into a continuous distillation unit 12 operated at a head temperature of about 60°–80° C. and pressures ranging from 10–20 psia to distill off from the LPO product the major part of the volatile light ends which are removed from distillation unit 12 via line 14. The light ends removed via line 14 include MVK and MIPPK as well as other light carbonyl compounds. The bottoms removed from distillation unit 12 via line 16 comprise the acid products as well as the reaction products of the unsaturated ketones and acids which are formed in the LPO reactor including the Michael adducts such as formed by the reaction of MVK and acetic acid. During butane oxidation, the bulk of the acid product comprise $C_1$–$C_4$ monocarboxylic acids. The base product via line 16 is directed via line 18 to a dehydration column 20 which operates at a head temperature and pressure sufficient to distill off water. Subatomspheric pressures are preferred. Water and other light ends including MVK and MIPPK are separated via line 22 from the LPO product. A base product again comprising the $C_1$–$C_4$ acid products and Michael adducts leave the base of dehydration column 20 via line 24. In the next stage of the process, formic acid is removed by directing the bottoms 24 to an additional light end removal tower 26 via line 28 which is operated at a temperature of 85°–110° C. and a pressure of from about 5–20 psia. Again, subatmospheric pressures are preferred. From the top of column 26, MVK, MIPPK, other light ends and formic acid are removed via line 30 while the acid products comprising acetic acid and heavier acids ($C_2$–$C_4$ acid products) as well as the Michael adducts are removed from the base of column 26 via line 32 for further purification as will be later explained. The distillate via line 30 containing about 60 wt. % formic acid and the bulk of the remainder water and acetic acid is directed to an acetic acid recovery tower 34 which is operated at a temperature 95°–120° C. Mixed with the distillate from column 26 entering acetic acid recovery tower 34 via line 30 is an extractant which removes the acetic acid from the formic acid and carries the acetic acid to the base of column 34 via line 36. The acetic acid stream can then be directed to further processing such as the anhydride furnace as discussed below. Distilled overhead acetic acid recovery tower 34 and leaving column 34 via line 38 is formic acid, and, again, light carbonyl compounds including the unsaturated MVK and MIPPK. These unsaturated and other light end carbonyls are removed from the formic acid via the formic acid tower 40 which receives the distillate 38 via line 42 and distills off the light ends including the unsaturated carbonyl compounds via line 44.

As can be seen, the unsaturated carbonyls including MVK and MIPPK are carried from the LPO reactor to the formic acid recovery system inasmuch as the Michael adducts and other reaction products of the unsaturated ketones and acids are carried as bottoms products from one distillation tower to the other whereby in each column, there is some reverse reaction in which the adducts are broken down thermally into the substituent carbonyl and acid components. The complete removal of these unsaturated compounds from the acid product is not readily achieved and, accordingly, prior to this invention there was always some of these unsaturated compounds in the final acid product which if present in excessive amounts adversely affected the quality of the acid as characterized by permanganate time.

Not only is the formic acid adversely affected by the presence of the unsaturated compounds, higher acids such as acetic acid, propionic acid, butyric acid, etc. are also adversely affected. This can be seen by further following the purification scheme as set forth in the FIGURE. Thus, the bottoms from the light end removal column 26 is removed via line 32 and directed to high boiler column 46 via line 48 and is distilled to remove the acetic acid from the heavier acid components including any of the Michael adduct products which may be present. The higher acid components leave the high boiler column 46 via line 50 for further treatment. The acetic acid is distilled from column 46 and is directed via line 52 to further processing and purification to an acetic acid which will meet commercial specifications. Specifically, the acetic acid distillate (greater than 95 wt. % acetic acid) via line 52 can be directed via line 54 to furnace 56 wherein the distillate is heated to dehydrate the acetic acid to form acetic anhydride. Alternatively or simultaneously, the acetic acid distillate via line 52 can be directed via line 58 to reduction unit 60 where the distillate is treated with hydrogen so as to hydrogenate the unsaturated carbonyl compounds which degrade the permanganate time of the acetic acid. The crude acetic acid product which has been hydrogenated to convert the methyl vinyl ketone and methyl isopropenyl ketone to methyl ethyl ketone and methyl isopropyl ketone, respectively, in reduction unit 60 leaves via line 62 and is directed to the final purification tower 64 via line 66 to produce an acetic acid product which will meet commercial specifications and which leaves column 64 via line 68. Distilled off via line 67 are the lower carbonyl compounds including the unsaturated and saturated ketones. A residue stream comprising heavy carbonyl compounds, heavier acids and any remaining Michael adducts are taken from the bottoms via line 70.

As in the final recovery of formic acid, unsaturated carbonyls and the Michael adducts are carded downstream during the purification of the acetic acid and higher acid components. Thus while many of the Michael adducts are removed as bottoms 50 from the higher boiler column 46, the reverse reaction produces small amounts of the MVK and MIPPK which leave with the acetic acid via line 52 and eventually into the reduction unit and specification acetic acid at column 64. Thus, it has been found that Michael adducts and the unsaturated carbonyl compounds are present throughout the purification system starting with the LPO reactor to the specification acid columns. If present in excessive amounts, these unsaturated carbonyl compounds as previously stated degrade the quality of the acids with respect to the permanganate time which is an important characteristic in determining the commercial viability of the acid products.

In accordance with the present invention, a catalyst is utilized to break down the Michael adducts into the substituents thereof, i.e., unsaturated carbonyls and acids, during the early stages of the purification process so as to allow removal of such lighter unsaturated carbonyl compounds during the initial stages of purification. Since the Michael adducts are substantially broken down early in the process, only a small portion of these adducts are carded downstream. Consequently, thermal breakdown of the remaining adducts results in only minor amounts of the undesired unsaturated carbonyl compounds from being carried into the purified acid streams. While either a basic or acidic catalyst can catalyze the breakdown of the Michael adducts, in the acidic environment of the LPO reaction products, a basic catalyst would be soon neutralized and inactivated. Accordingly, it is preferred to use an acid catalyst to catalyze the breakdown of the Michael adducts. The preferred catalysts are strong acid catalysts including, for example, sulfonic acid catalysts and mineral acids such as hydrochloric acid, phosphoric acid, sulfuric acid, etc. Methane sulfonic acid and benzene sulfonic acid have been found particularly useful in breaking down the Michael adducts.

It is preferred to add the catalyst to the purification system prior to the recovery of any acid product. Specifically, adding the catalyst to the dehydration column 20 or the light end removal column 26 provides sufficient breakdown of the adducts into their substituent components, allows removal of the unsaturated carbonyl compounds, and at the same time prevents substantial amounts of the Michael adducts from being discharged downstream into the formic acid, acetic acid and heavier acid purification schemes. The amount of the catalyst added to the respective columns will typically be between about 0.02–1 wt % of column liquid with the preferred ranges being about 0.02–0.2 wt %. Higher levels of the catalyst may be corrosive to the distillation equipment and, as such, corrosion at higher catalyst levels should be carefully monitored.

It has been found that up to 90% and more of the Michael adducts can be broken down to allow the removal of the lighter unsaturated ketones overhead the column in which the acid catalyst is added. Other benefits of the addition of the acid catalyst is a substantial conversion of acetoin to biacetyl. Such conversion reduces the amount of colored bodies in the final specification acid and can further reduce the amount of potassium permanganate added to the acid to obtain the desired acid purity. Additional hydrolysis of esters such as butyl acetate to the respective alcohols and organic acids (butanol and acetic acid) reduces the ester impurities such as butyl acetate in the specification acetic acid and at the same time recovers additional amounts of the organic acids.

The acid catalyst is preferably added to the purification system at dehydration column 20 and allowed to be carded downstream to light end removal column 26 and even to the high boiler tower 46 prior to being neutralized. Most preferably, the catalyst should be neutralized prior to reaching the high boiler column 46. Neutralization can simply be achieved by adding a base such as an alkali metal hydroxide, e.g. KOH to the liquid stream carrying the catalyst.

EXAMPLE I

Three catalysts were tested in this example. Methane sulfonic acid (MSA), phosphoric acid and benzene sulfonic acid (BSA).

A 40 tray Oldershaw glass column was run using three different operating conditions. The first operating condition simulated dehydration column 24 on total reflux for one hour. After refluxing, 10% of the sample was taken overhead at a reflux ratio of 1:1. All three catalysts were tested under this operating condition. The second operating condition simulated dehydration column 24 with a continuous takeoff of overhead product for two hours. The phosphoric acid and BSA were tested under this operating condition.

The third operating condition simulated three towers, 20, 26 and 46. Each tower was run with a continuous takeoff of overhead product for two hours. This operating condition was only used with the BSA catalyst. The purpose of simulating these three towers was to determine the percent breakdown of Michael adducts through high boiler tower 46.

For the first operating condition, 850 g of residue from line 24 and the appropriate amount of catalyst were charged to the column. After one hour of total reflux, 85 mls of material were taken overhead at a reflux ratio of 1:1. The 85 mls were analyzed by GC-MS to determine the mount of unsaturated compounds, (MVK, MIPPK) produced. These results were compared to the blank run in which no catalyst was added.

For the second operating condition, 850 g of residue from line 24 and the appropriate amount of catalyst were charged to the column. After the material began to boil, the reflux ratio was set to remove 85 mls of material overhead in 2 hours. The overhead product was analyzed by GC-MS to determine the amount of unsaturated compounds produced. The results were compared to the blank and to the results of the first condition.

For the third condition, 1700 g of residue from line 24 were added to the column with the appropriate amount of catalyst. The reflux ratio was set for 450 mls of overhead product in two hours. After two hours, the residue was allowed to cool down. After complete cooling, the residue was reheated to simulate tower 26. The reflux ratio was set for 400 mls of overhead product in two hours. The residue was then cooled down again. After complete cooling, the residue was reheated to simulate tower 46. The reflux ratio was set for 600 mls of overhead in two hours. Each overhead product was analyzed to determine the amount of unsaturated compounds present. These results were compared to the blank and the results from the two previous operating conditions.

The third condition was also used with a feed made to simulate the feed to tower 20. The top temperature of the tower was used instead of overhead volumes because of the inconsistencies of the feed compositions. For the cut from simulated column 20, product was taken overhead until the top temperature was 101.0° C. This amounted to approximately 450 mls of product. The maximum top temperature for the second cut was 112° C., and approximately 570 mls of product taken overhead. For the third cut, approximately 500 mls of product was taken overhead with a top temperature of 115° C. The overhead product was analyzed by GC-MS to determine unsaturated compounds and compared to the blank.

TEST RESULTS

The results of the three catalysts used in this experiment are listed below. A blank (no catalyst added) was run each time new feed samples had to be taken.

MSA CATALYST

MSA was only used with the first operating condition. Two catalyst concentrations were tested, 0.05 wt % and 0.2 wt %. Both MSA concentrations caused break down of the Michael adducts (see Table 1). However, to obtain the best results, 0.2 wt % MSA concentration was needed.

TABLE 1

| WT % MSA | ppM MVK | ppM MIPPK |
|---|---|---|
| 0 (Blank) | 780 | 950 |
| 0.05 | 1396 | 3743 |
| 0.2 | 2821 | 10721 |

All MSA catalyst tests were run on one hour total reflux.

PHOSPHORIC ACID CATALYST

Phosphoric acid was chosen for low cost and low corrosion. It was used for the first and second operating conditions. 0.2 wt % phosphoric acid catalyst concentration was tested first for comparison to the 0.2 wt % MSA catalyst concentration. At this concentration little break down of the Michael adducts occurred (see Table 2). To improve Michael adduct break down, 0.5 wt % phosphoric acid was tested. This concentration did not cause as much breakdown as the 0.2 wt % phosphoric acid.

After the 0.5 wt % phosphoric acid sample was run on total reflux for 1 hour and 10% taken overhead, the sample was run on total reflux for 2 additional hours and another 20% was taken overhead. The 2 hours total reflux sample had more MIPPK and MVK than the 1 hour reflux sample. This indicated that the MIPPK and MVK were in equilibrium with their Michael adducts in the first condition. It was decided to test a continuous takeoff of overhead product. This would remove the light ends and convert more of the Michael adducts to their unsaturated form to remain in equilibrium. 0.2 wt % phosphoric acid was used for the continuous takeoff. More MIPPK and MVK were present in the overhead product than in the 1 hour total reflux. This catalyst was still not as effective as the MSA catalyst was on total reflux. A stronger acid than phosphoric acid is thus preferred to break down the Michael adducts, but such catalyst should not be so strong that it causes corrosion problems.

TABLE 2

| WT % PHOSPHORIC ACID | TOTAL REFLUX TIME | ppM MVK | ppM MIPPK |
|---|---|---|---|
| 0 (Blank) | 1 hour | 780 | 950 |
| 0.2 | 1 hour | 2855 | 3485 |
| 0.5 | 1 hour | 2728 | 2507 |
|  | then 2 additional hours | 1779 | 4525 |
| WT % PHOSPHORIC ACID | CONTINUOUS TAKEOFF | ppM MVK | ppM MIPPK |
| 0 (Blank) | 2 hour | 860 | 1000 |
| 0.2 | 2 hour | 2200 | 4800 |

BSA CATALYST

This acid is slightly weaker than MSA but stronger than phosphoric acid. It is also not as corrosive nor as expensive as MSA. 0.05 wt % BSA was used to compare with the 0.05 wt % MSA results on total reflux. The BSA catalyst actually caused more breakdown of the Michael adducts than MSA (see Table 3). The 2 hour continuous takeoff with 0.05 wt % BSA gave the best results yet. 35000 ppm MIPPK and 11400 ppm of MVK were present in the overhead.

Several runs with 0.03 wt % BSA were tested using condition three (see Table 3). A final three runs were performed to determine the percent breakdown of the Michael adducts and where to neutralize the catalyst. Table 3 sets out the conditions and results.

TABLE 3

| WT % BSA | TOTAL REFLUX TIME | ppM MVK | ppM MIPPK |
|---|---|---|---|
| 0 (Blank) | 1 hour | 780 | 950 |
| 0.05 | 1 hour | 3586 | 8162 |

| WT % BSA | CONTINUOUS TAKEOFF | ppM MVK | ppM MIPPK |
|---|---|---|---|
| 0 (Blank) | 2 hours | 860 | 1000 |
| 0.05 | 2 hours | 11396 | 35677 |
| 0.03 | 2 hours | 11427 | 13344 |

| Tower WT % | 20 | | 26 | | 46 | |
|---|---|---|---|---|---|---|
| BSA | MVK | MIPPK | MVK | MIPPK | MVK | MIPPK |
| 0 (Blank) | 1343 | 530 | 632 | 370 | 867 | 700 |
| 0.03 | 7085 | 4255 | 4866 | 4001 | 667 | 587 |
| 0.03 | 7993 | 5023 | 1499 | 940 | 425 | 300 |
| | | | | | (catalyst neutralized) after 26 | |
| 0 (Blank) | 1543 | 834 | 1091 | 578 | 975 | 865 |
| 0.03 | 5680 | 3017 | 1560 | 1300 | 400 | 200 |
| | | | | | (catalyst neutralized) after 26 | |
| 0 (Blank) | 1956 | 1961 | 919 | 420 | 670 | 430 |
| 0.03 | 8208 | 18870 | 522 | 887 | <100 | <100 |
| | | | | | (catalyst neutralized) after 20 | |
| 0.03 | 8200 | 19000 | 495 | 300 | 145 | 82 |
| | (catalyst neutralized after 20) | | | | | |

EXAMPLE 2

The purpose of this test was to determine the maximum breakdown of the Michael Adducts with a consistent flow of benzene sulfonic acid (BSA) into the base of the dehydration tower 20 at the Pampa, Tex., LPO plant. A first test did not have a consistent flow of BSA and therefore only 40% breakdown of the Michael Adducts was achieved. Also, the BSA was fed into the feed line of column 20 in the first test. During this second test, the B SA was fed into the base of column 20.

A 55 gallon drum of 70 wt % benzene sulfonic acid was transferred into the same flowcases used during the first BSA test. The BSA was pressured out of the flowcases through ½ inch tubing to a nozzle located just above the liquid level in the tower base. The BSA was metered through a 0–30 GPH rotameter at a rate of 2 GPH (20 pph). 5 gal of BSA was added in the first thirty minutes to quickly bring the base concentration to 0.05 wt % BSA. This allowed Michael adduct breakdown to reach steady-state faster and therefore, gave more data points at each conversion. The rotameter had to be readjusted every 10 minutes to insure a consistent flow of BSA. The flow was verified by gauging the flowcases using a strapping table. Tables 4 and 5 set forth the results of testing. Table 4 set out the concentration of Michael adducts (4-acetoxy-2-butanone) in the column residue as a measure of conversion.

TABLE 4

A "—" means the sample was not checked for that particular component. "N.D." means it was not detected.

| Time | Date | ppm 4a2b | breakdown | conversion | wt % PSA |
|---|---|---|---|---|---|
| 12 p.m. | Day 1 | 1000 | N/A | N/A | N/A |
| 7 a.m. | Day 2 | 1200 | N/A | N/A | N/A |
| 11 a.m. | Day 2 | — | — | 54% | 0.06 |
| 1 p.m. | Day 2 | 700 | 42% | 57% | 0.077 |
| 4 p.m. | Day 2 | 700 | 42% | — | 0.082 |
| 6 p.m. | Day 2 | 650 | 46% | — | — |
| 8 p.m. | Day 2 | 515 | 58% | — | 0.066 |
| 11 p.m. | Day 2 | 540 | 56% | 68% | 0.126 |
| 2 a.m. | Day 3 | 515 | 58% | — | — |
| 4 a.m. | Day 3 | 500 | 59% | — | — |
| 6 a.m. | Day 3 | 330 | 73% | 43% | — |
| 8 a.m. | Day 3 | 340 | 73% | 55% | 0.005 |
| 2 p.m. | Day 3 | 910 | 24% | — | N.D. |
| 11 a.m. | Day 4 | 1100 | 8.3% | 48% | N.D. |
| 9 a.m. | Day 8 | 1130 | N/A | N/A | N.D. |

TABLE 5

Overhead MVK and MIPPK during the PSA test.

| Time | Date | ppm MVK | ppm MIPPK |
|---|---|---|---|
| 7 a.m. | Day 2 | 866 | 417 |
| 11 a.m. | Day 2 | 1464 | 1460 |
| 2 p.m. | Day 2 | 1700 | 1251 |
| 4 p.m. | Day 2 | 1732 | 1169 |
| 8 p.m. | Day 2 | 2165 | 1376 |
| 11 p.m. | Day 2 | 1329 | 1041 |
| 4 a.m. | Day 3 | 2598 | 1668 |
| 7 a.m. | Day 3 | 1299 | 604 |
| 2 p.m. | Day 3 | 914 | 460 |
| 9 a.m. | Day 8 | 1099 | 460 |

What is claimed is:

1. A method of purifying an oxidate product formed by the liquid phase oxidation of a $C_4$–$C_8$ paraffinic hydrocarbon, said oxidate product comprising carboxylic acids and the reaction products of unsaturated carbonyls and said carboxylic acids, said method comprising removing from said oxidate product said reaction products by adding a sulfonic acid catalyst to said oxidate product so as to break down said reaction products to separate unsaturated carbonyl and carboxylic acid components and distilling said unsaturated carbonyls from said carboxylic acids.

2. The method of claim 1 wherein said sulfonic acid catalyst comprises methane sulfonic acid or phenyl sulfonic acid.

3. The method of claim 1 wherein said oxidate product further comprises water, directing said oxidate product to a dehydration column to distill off said water and said unsaturated carbonyls and form a residue comprising carboxylic acids.

4. The process of claim 3 wherein said catalyst is added to the oxidate product contained in said dehydration column.

5. The process of claim 3 wherein said catalyst is added to the residue of said dehydration column.

6. The method of claim 1 wherein said oxidate product is formed by the liquid phase oxidation of butane and further comprises water, feeding said oxidate product to a dehydration column to distill off water and said unsaturated carbonyls and form a residue comprising carboxylic acids, said carboxylic acids comprising $C_1$–$C_4$ carboxylic acids, feeding said residue to a second distillation column to separate as distillate said $C_1$ carboxylic acids from a bottoms comprising said $C_2$–$C_4$ carboxylic acids, adding said catalyst to said dehydration column, said second distillation column, or both.

7. The process of claim 6 wherein said catalyst is added to the oxidate product being fed to said dehydration column.

8. The process of claim 6 wherein said catalyst is added to said dehydration column.

9. The method of claim 6 wherein said catalyst is added to said residue being fed to said second distillation column.

10. The method of claim 6 wherein said catalyst is added to said second distillation column.

11. The method of claim 1 wherein subsequent to said break down of said reaction products, said catalyst is neutralized.

12. The method of claim 11 wherein said catalyst is neutralized by adding a base to said oxidate product.

13. The method of claim 6 wherein subsequent to said break down of said reaction products, said catalyst is neutralized.

14. The method of claim 13 wherein said catalyst is added to said dehydration column and said catalyst is neutralized by adding a base to said residue or said second distillation column.

15. The method of claim 13 wherein said catalyst is neutralized by adding a base to said bottoms.

* * * * *

UNITED STATES PATENT AND TRADEMARK OFFICE
CERTIFICATE OF CORRECTION

PATENT NO. : 5,516,406

DATED : May 14, 1996

INVENTOR(S) : Nicole G. Wallace; Kenneth A. Windhorst

It is certified that error appears in the above-identified patent and that said Letters Patent is hereby corrected as shown below:

In column 3, line 41, replace "... carded ..." with --carried--.
In column 3, line 50, replace "... carded ..." with --carried--.
In column 5, line 47, replace "... carded ..." with --carried--.
In column 6, line 3, replace "... carded ..." with --carried--.
In column 6, line 49, replace "... carded ..." with --carried--.
In column 7, line 14, replace "... mount ..." with --amount--.

Signed and Sealed this

Twenty-second Day of October, 1996

Attest:

BRUCE LEHMAN

Attesting Officer     Commissioner of Patents and Trademarks